(12) United States Patent
Jestrabek-Hart

(10) Patent No.: US 6,979,303 B2
(45) Date of Patent: Dec. 27, 2005

(54) ARM SLING APPARATUS ALLOWING MOVEMENT OR TOTAL IMMOBILIZATION

(76) Inventor: Bernadette Jestrabek-Hart, 3175 N. Ten Mile Rd., Meridian, ID (US) 83642

( * ) Notice: Subject to any disclaimer, the term of this patent is extended or adjusted under 35 U.S.C. 154(b) by 0 days.

(21) Appl. No.: 10/653,855

(22) Filed: Sep. 2, 2003

(65) Prior Publication Data

US 2005/0020950 A1  Jan. 27, 2005

Related U.S. Application Data

(60) Provisional application No. 60/407,448, filed on Aug. 30, 2002.

(51) Int. Cl.[7] ............................. A61F 5/00; A61F 5/02
(52) U.S. Cl. ................... 602/4; 602/20; 2/45
(58) Field of Search ............... 602/4, 20, 5, 60–62; 2/44, 45

(56) References Cited

U.S. PATENT DOCUMENTS

| | | | |
|---|---|---|---|
| 9,828 A * | 7/1853 | Day ............................ | 602/4 |
| 2,358,551 A | 9/1944 | Beaton ........................ | 227/49 |
| 4,214,579 A | 7/1980 | Ford ........................... | 128/94 |
| 5,413,552 A * | 5/1995 | Iwuala ......................... | 602/4 |
| 5,464,383 A | 11/1995 | Padden et al. .............. | 602/20 |
| 5,746,705 A | 5/1998 | Sheppard ..................... | 602/4 |
| 5,830,165 A | 11/1998 | Rowe et al. ................. | 602/4 |
| 6,306,111 B1 | 10/2001 | Dean ........................... | 602/20 |
| 6,406,449 B1 | 6/2003 | Moore et al. ................ | 602/4 |
| 6,634,923 B2 * | 10/2003 | Waitz .......................... | 450/86 |
| 2004/0215119 A1 * | 10/2004 | Avon ........................... | 602/4 |

* cited by examiner

*Primary Examiner*—Kim M. Lewis
(74) *Attorney, Agent, or Firm*—Pedersen & Co., PLLC; Ken J. Pedersen; Barbara S. Pedersen

(57) ABSTRACT

An arm sling apparatus includes cooperating suspension system and support frame wherein the weight of a user's arm may be transferred from the shoulder to the torso. The arm sling apparatus allows the shoulder to rest and/or heal by temporarily relieving the shoulder of its lifting duties preferably without touching and therefore without stressing or fatiguing the neck or shoulder regions. A suspension system comprising one or more suspending devices engages and supports the arm in conjunction with a rigid, stable support frame from which it is hung. The support frame preferably comprises a stiff, but comfortable, waist belt and a rigid upright support arm adapted to accept the weight applied to the suspension system and center this weight about the hips. The support frame provides sufficient clearance for the shoulder and neck regions so that pressure is not applied to these areas. Immobilization straps or other devices may be adjusted to permit varying degrees of activity or immobilization so that the shoulder corresponding to the suspended arm may rest and/or heal. The device may also be used to prevent repetitive wear injuries if a user finds him or herself performing the same motion repeatedly.

21 Claims, 7 Drawing Sheets

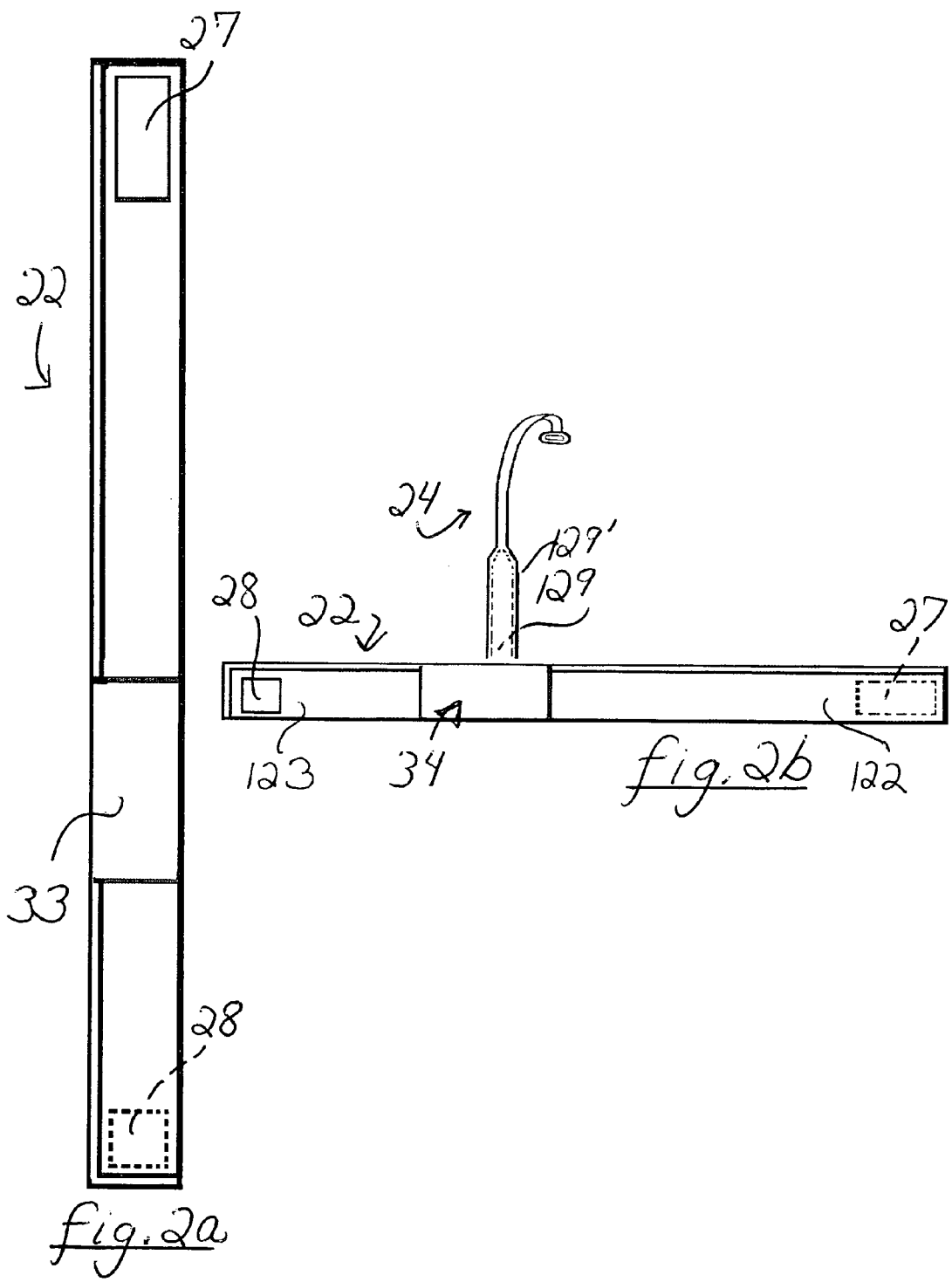

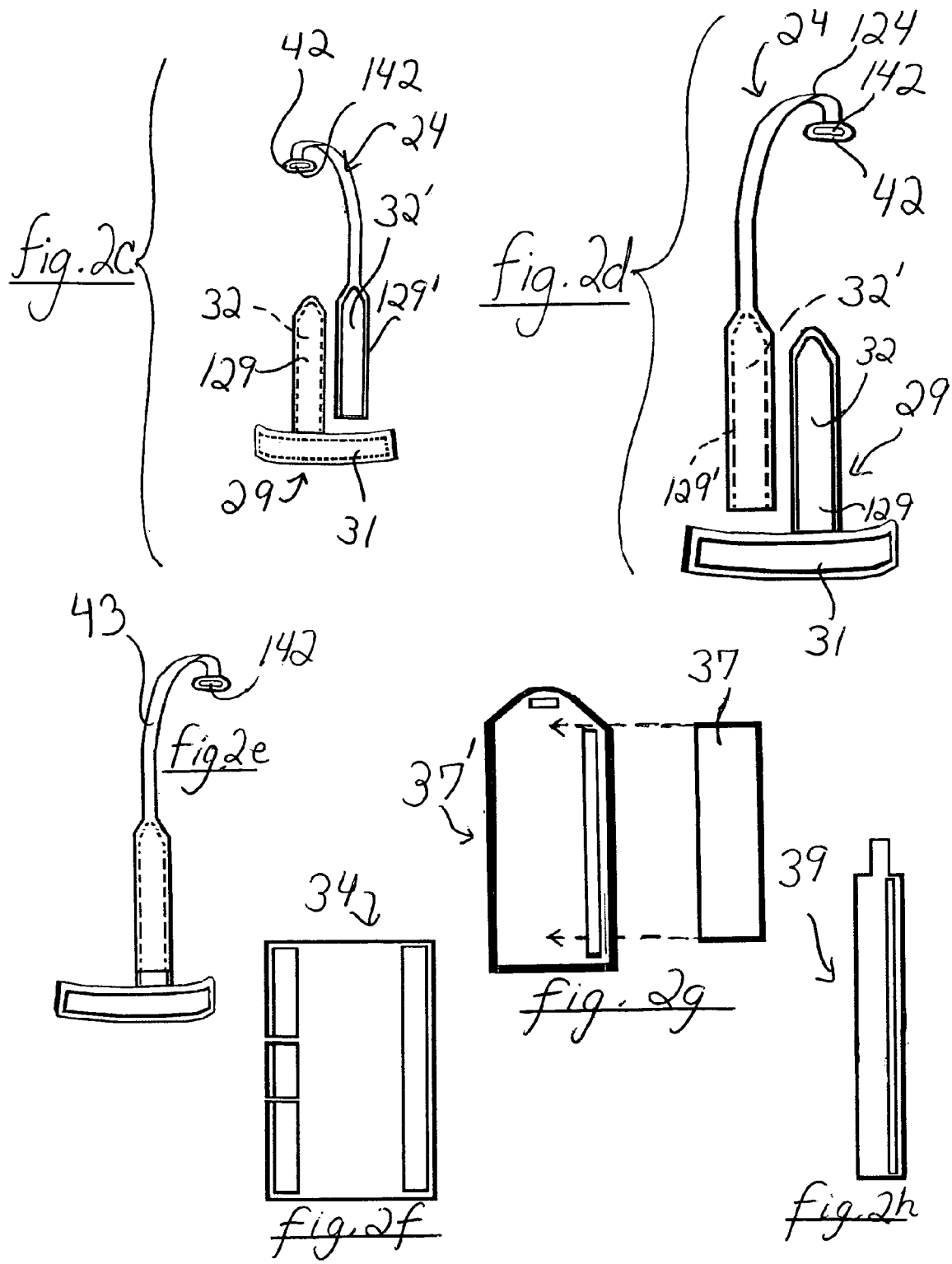

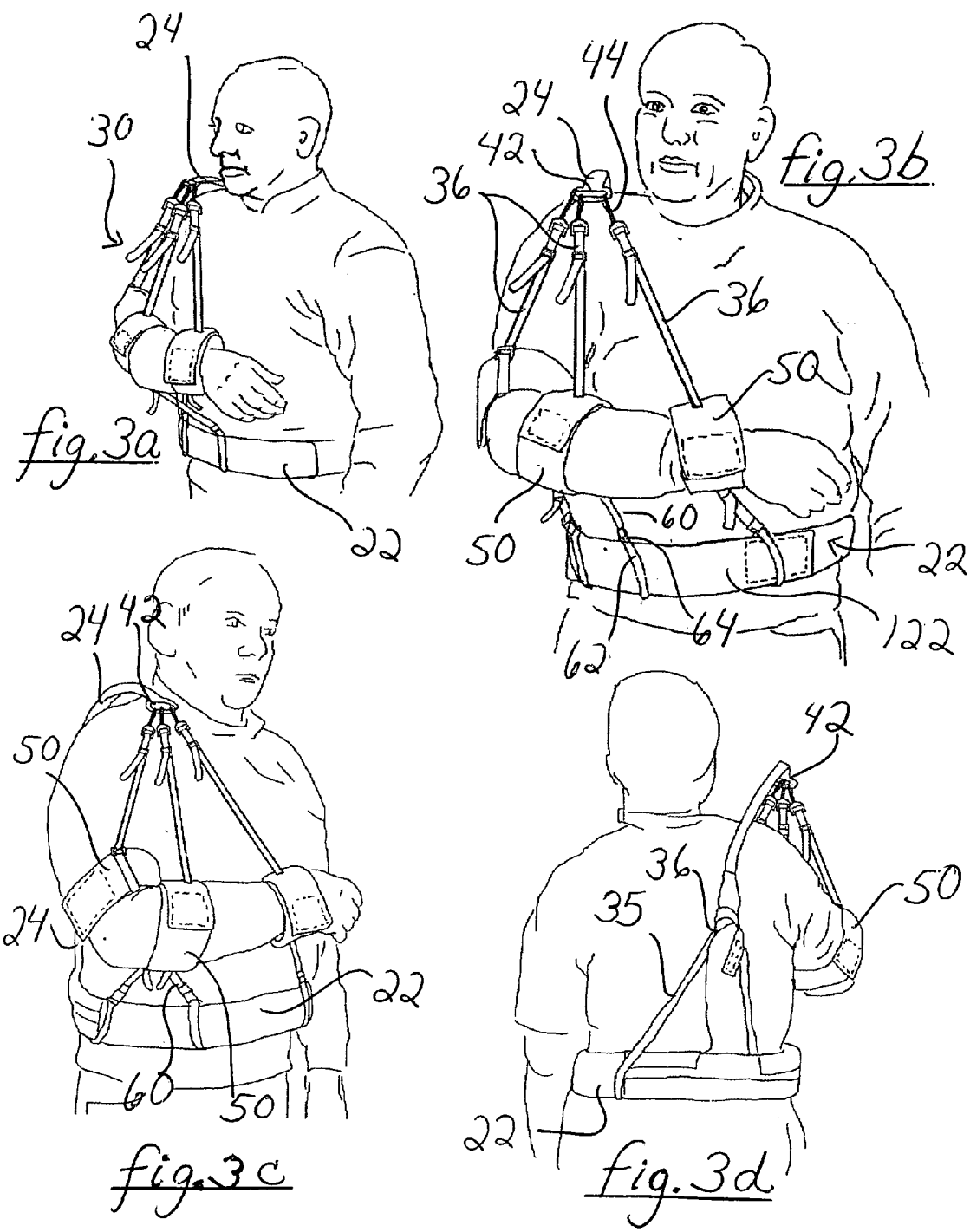

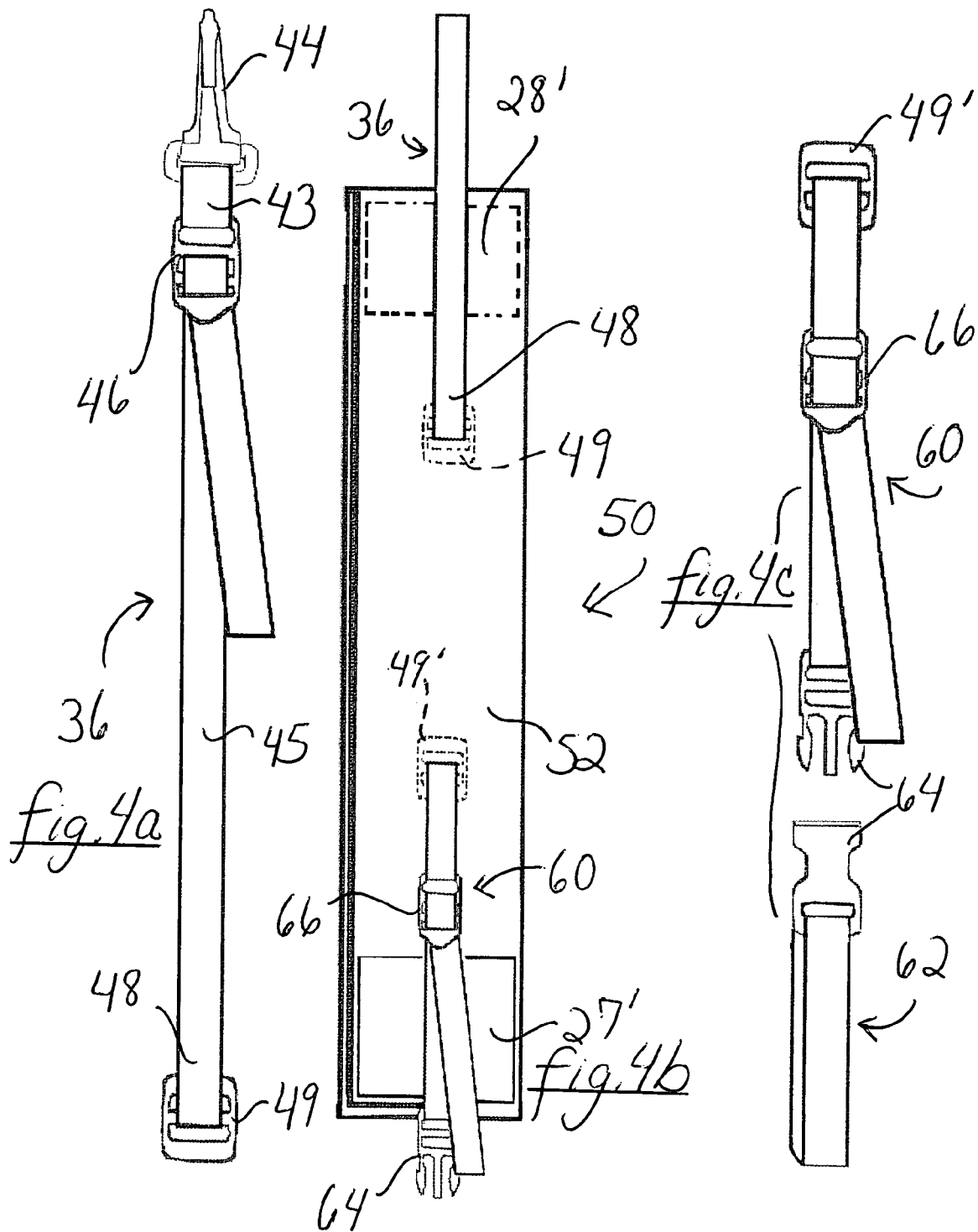

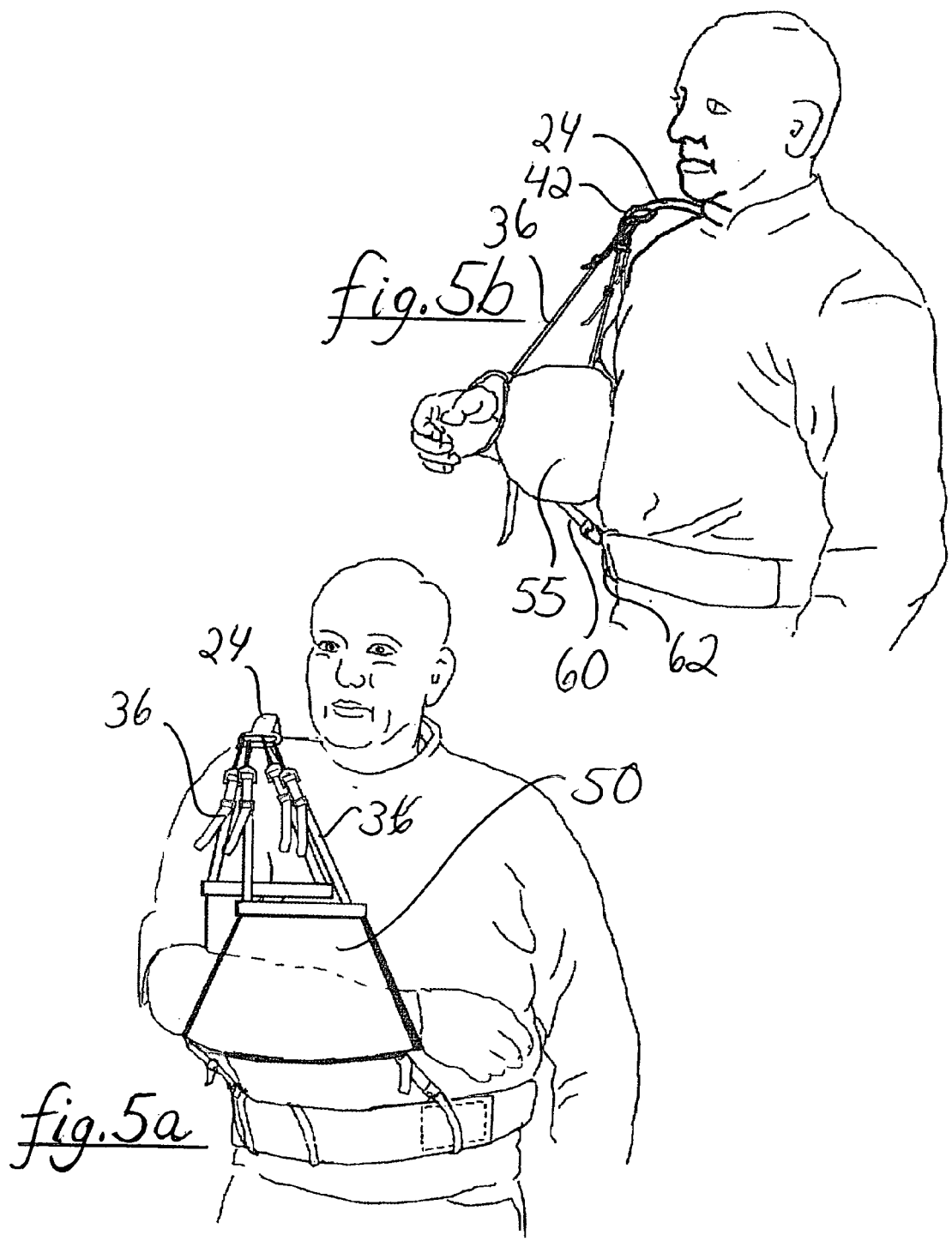

ARM SLING APPARATUS ALLOWING MOVEMENT OR TOTAL IMMOBILIZATION

This application claims priority from U.S. Provisional Patent Application Ser. No. 60/407,448, entitled "Arm Sling Allowing Movement or Total Immobilization," which was filed on 30 Aug. 2002, the disclosure of which is herein incorporated by reference.

BACKGROUND OF THE INVENTION

1. Field of the Invention

The present invention relates generally to medical and surgical equipment. More specifically, the invention relates to an arm sling for supporting the weight of an arm, which may be adjusted to allow movement or total immobilization. More specifically, the invention relates to relief of shoulder stresses involved in bearing the weight of the arm or holding the arm in a generally upright position.

2. Related Art

Typically, the shoulder bears substantially the full weight of the arm. However, sometimes this load must be minimized or eliminated, using various devices, to allow an injured shoulder to heal or to prevent further damage. An example of such a situation would be the period of recovery following surgical repair of the rotator cuff. A device used to support the weight of the arm and/or any additional weight held by the arm can also be used to keep the shoulder from becoming over-strained and thus allow the shoulder and/or arm to heal. An example of this is the Ultimate Arm Sling®, the Open Envelope Arm Sling or Envelope Arm Sling by Best Orthopedic, and the Perfect Fit Arm Sling by Johnny Sheppard. The healing of some injuries requires that movement of the arm be severely limited or even that the arm be completely immobilized. Restricting movement of the arm promotes rest and prevents further damage to bones or body tissues in the injured area(s). One device that may be used in such cases is a sling that goes under and around the arm and then extends up and around the neck, which sling will support and bear the weight of the arm. In those cases requiring that the arm be immobilized in close proximity to the body, an additional strap or swath can be placed around the arm and around the body, thus, holding the arm against the body and limiting motion. Examples of this type of sling include The Joslin Swathe™, Acromioclavicular Splint, the Breg Slingshot, or The Shoulder Immobilizer by Darco. Similarly, U.S. Pat. No. 5,830,165 (Rowe et al.) discloses a sling-like swathe wherein a band of flexible material is wrapped beneath the arm, up and over the shoulder, and around the body to both support the weight of the arm and constrain the arm against the body of the wearer. Other designs also permit the immobilization of an injured arm. For example, U.S. Pat. No. 6,406,449 (Moore et al.) provides an arm supporting cuff in a vest. In this example, insertion of the injured arm into the cuff substantially supports the weight of the arm and holds the arm against the body of the wearer.

Still, there remains a need for an arm sling apparatus capable of bearing the weight of the arm and transferring this load to a stronger, more stable part of the body to prevent further injury. It is an object of the present invention to provide an arm sling apparatus wherein the weight of the arm may be temporarily removed from the shoulder to allow the shoulder to rest and/or heal. It is a further object of the present invention to furnish a device that may support the shoulder's typical load comfortably without stressing or fatiguing the neck or shoulder regions.

SUMMARY OF THE INVENTION

The present invention comprises a sling apparatus for supporting and/or anchoring an injured arm relative to a wearer's body. The sling apparatus comprises a support frame and suspension system that cooperate to lift the user's arm and transfer the weight of the user's arm from the shoulder to the hips and/or waist and/or back. Preferably, the sling apparatus comprises a rigid or semi-rigid support arm that curves over the user's shoulder from a waste or hip belt, the support arm being adapted to connect to and support at least a portion of the user's arm. This way the weight of the user's arm may be supported by and, in effect, transferred to the user's body core, that is, the middle and/or lower torso, rather than the shoulder and/or neck areas. Further securement systems may be provided that limit or totally restrain movement of the arm relative to the rest of the user's body.

In the preferred embodiment, the support frame comprises a waist belt, and a rigid support arm that attaches to the belt via a rigid connector integral with or firmly anchored on the belt. The waist belt is preferably a padded band fully encircling the waist just above the hips that is adapted to accept the weight of the arm which is suspended from the support arm. The connector is sewn into, made integral with, or otherwise adhered to the belt to secure and stabilize the upright support arm. In the preferred embodiment, the connector comprises a thin, flat, generally hemispherical plate that conforms to the contours of the user's back. The upright arm extends generally over the shoulder of the wearer from about the middle-back of the belt or alternatively from the right or left back areas to a position above the shoulder corresponding to the arm being suspended. Preferably, the configuration of the support frame allows sufficient isolation of the load-bearing components of the sling apparatus from the neck and shoulder regions so that any pressure in these neck and shoulder regions is minimal. Most preferably, the invented apparatus has no contact with, and does not apply any pressure to, the neck and shoulder regions.

BRIEF DESCRIPTION OF THE DRAWINGS

FIGS. 2a–e are views of the various components forming one embodiment of the support frame of the arm sling apparatus of FIG. 1. FIG. 2a is a view of one embodiment of a waist/hip belt shown unhooked and flattened. FIG. 2b illustrates a support arm in a position on the belt that places the support arm at a rear-right position on the user's back, to leave a longer right belt end for wrapping fully across the user's front from right to left. FIG. 2c is an exploded front view of the pieces-parts of the support arm system, including a connector that attaches to the belt of FIGS. 2a and 2b and the support arm that attached to the connector. FIG. 2d is an exploded rear view of the pieces-parts of FIG. 2b. FIG. 2e is a rear view of the pieces-parts of FIG. 2c and 2d connected together. FIG. 2f illustrates one embodiment of padding/cover that may be wrapped around the combination of the support arm lower portion and the lower portion of the connector (when connected as shown in FIG. 2e), and the belt. FIG. 2g illustrates one embodiment of a gel pack/padding and a wrap/cover that may be connected to a portion of the support arm. FIG. 2h illustrates one embodiment of an optional cover for the upper portion of the support arm.

FIG. 3a is a side, perspective view of the arm support system of FIG. 1 as seen from the side opposite the injured arm.

FIG. 3b is a front, perspective view of the arm support system of FIG. 1 demonstrating one method of anchoring the arm to the waist belt.

FIG. 3c is a side, perspective view of the arm support system of FIG. 1 as seen from the side adjacent the injured arm.

FIG. 3d is a rear, perspective view of the arm support of FIG. 1.

FIGS. 4a–c are plan views of the various components forming one embodiment of a suspension and immobilization assembly according to the arm sling apparatus of FIG. 1. FIG. 4a illustrates one embodiment of a suspension strap. FIG. 4b illustrates one embodiment of a cuff for encircling a user's arm. FIG. 4c illustrates one embodiment of an immobilization strap including a sliding strap for use on a waist belt.

FIG. 5a is a perspective view of the arm sling of FIG. 1 showing an alternative suspension system with a broad sling member, as opposed to the narrower cuffs of FIGS. 1–5.

FIG. 5b is a perspective view of the arm sling apparatus of FIG. 1 showing an alternative means of anchoring the injured arm relative to the body in use with a pillow.

In FIG. 6a, two cuffs are used with a single lengthened restraining/immobilization strap. In FIG. 6b, a single cuff is used near the elbow allowing lateral movement of the forearm generally around a pivot point represented by the cuff and restraining/immobilization strap. In FIG. 6c, the restraining/immobilization strap is adjusted to allow the user to carry an item with only moderately-restrained movement. In FIG. 6d, the restraining/immobilization strap is shortened to allow the user to use a welding torch with the elbow restrained from upward motion but the arm substantially free to pivot at the elbow, and with the welding hose attached to the support arm so that the support arm bears much of the weight of the hose.

DESCRIPTION OF THE PREFERRED EMBODIMENTS

In the preferred embodiment of the invented sling apparatus, an eyelet or connectors positioned above the shoulder provides the point of attachment for the suspension system to the rigid support frame. Preferably, the eyelet is fixedly secured to the free end of the elongated support arm. The suspension system comprises one or more lifting/suspending devices adapted to lift the arm in cooperation with the support frame. In the preferred embodiment, adjustable suspension straps (elastic or inelastic) are removably attached at one end to the eyelet and fixedly secured at the other end to a plurality of cuffs adapted to encircle the arm. Preferably, three suspension straps are attached between the eyelet and the three cuffs (preferably, one strap per cuff) encircling the bicep, the forearm (adjacent the elbow) and the wrist. The suspension straps may then be tightened or loosened so that the weight of the arm is comfortably transferred to the hips and back via the support frame. Alternatively, a sleeve-like sling or other apparatus (rigid or flexible) may be hung from the rigid support to accept the injured arm. Transferring the weight of the arm (load) from the shoulder to the hips and back via support frame and suspension system minimizes and preferably eliminates stress and discomfort in the neck and shoulder regions and allows the arm and shoulder to rest and/or heal.

The sling apparatus may include means for further restricting or eliminating lateral and/or vertical movement of the arm. For example, the cuffs encircling the suspended arm may be anchored to the belt using straps, bands, wraps, or other fasteners to facilitate total, or near total, immobilization. These straps, bands or wraps may be tightened or loosened as necessary to facilitate varying degrees of activity or immobilization.

Referring now to the figures, several, but not the only, embodiments of the invented arm sling apparatus are illustrated. The arm sling of the present invention is designed to reliably support an arm without unnecessarily stressing or fatiguing the neck and/or shoulder regions. Rather, the invented sling relieves the shoulder of its lifting duties by transferring the load to the hips and back via a cooperating rigid support frame and suspension system. In the preferred embodiment, the load-bearing system is substantially isolated and preferably completely isolated from the neck and shoulder regions. As a result, the arm may be effectively immobilized, partially or completely, and the shoulder allowed to rest and/or heal.

Figure 1:
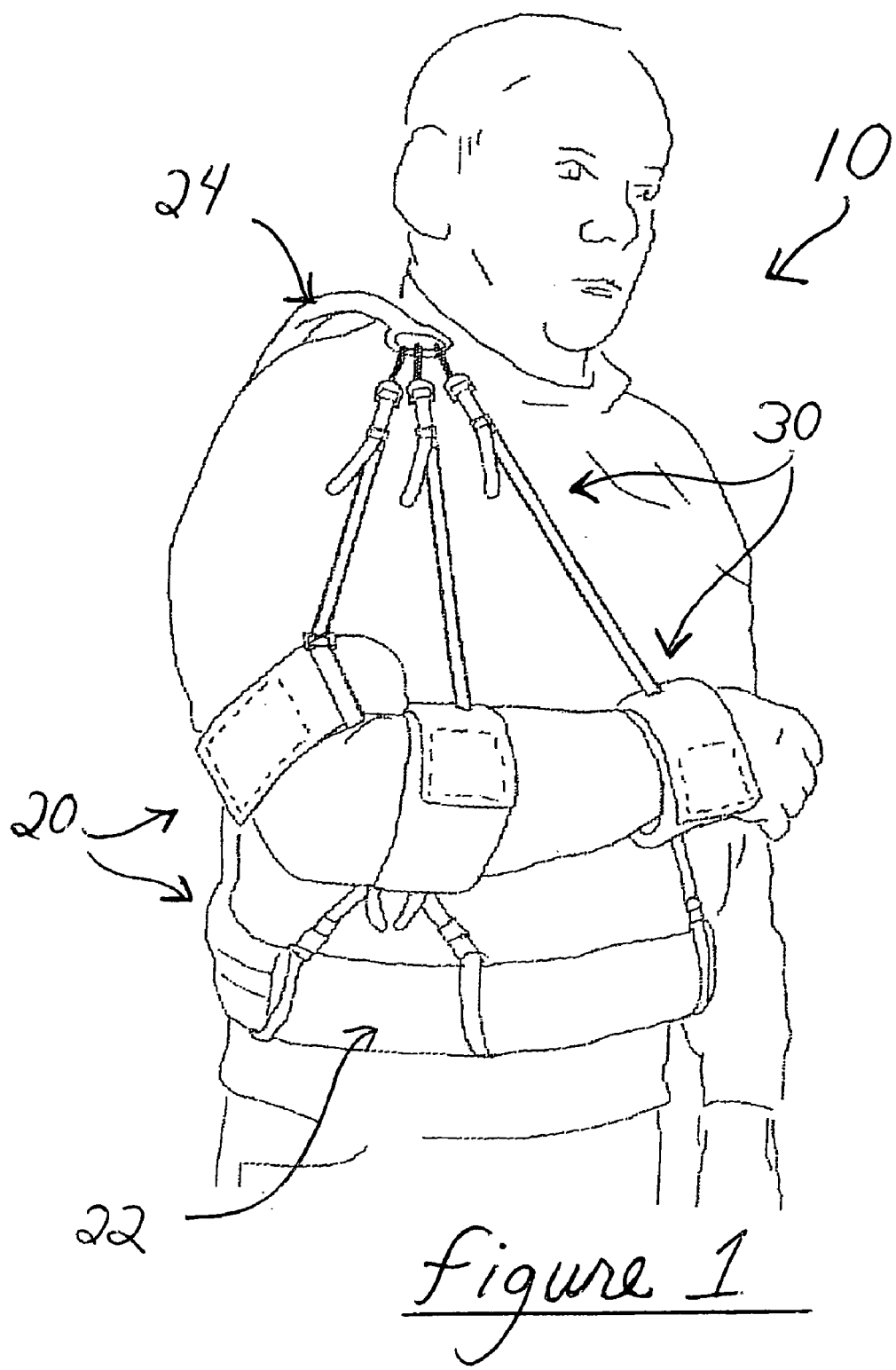
FIG. 1 is a front, perspective view of one embodiment of an arm sling according to the present invention in use on a person's right arm and waist.

As shown in FIG. 1, the invented arm sling apparatus 10 comprises a support frame 20 and a suspension assembly 30 adapted to lift the weight of the arm and hold the arm in a generally fixed position relative to the body of the wearer. Preferably, the support frame 20 of the invented apparatus comprises a waist belt 22 and an upright support arm ("upright support 24") through which the forces acting on the suspension system may be conveyed to the hips or lower back. In the preferred embodiment, load-bearing components of the arm sling apparatus 10 are substantially isolated from the shoulder and neck regions.

The waist belt 22 of the preferred support frame comprises a band of material that fully encircles the body of the user above the hips, as illustrated in FIG. 1. In other embodiments, the belt may be positioned elsewhere on the torso so long as the weight of the arm (applied to the support frame) is not supported by or at least substantially not supported by the neck or shoulder regions. Preferably, the band is padded according to conventional methods using foams, layered fabrics or other materials for comfort. The opposing ends of the waist belt may overlap to facilitate adjustment of the belt for various body sizes and/or shapes. Preferably, the belt is secured about the waist using a hook and loop closure system. In the preferred embodiment, the securement means comprises all or a substantial portion of the belt surface being loop material (or any material that receives and secures to the hook material) and at least one tab 28 of hook material secured to the belt at the outermost end. Preferably, a second tab 27 is provided on the opposite side from tab 28, so that the hook tabs on both ends of the belt may attach to the loop material substantially anywhere along the length of the belt. This way, the belt is wrapped around the user and secured, but it is easily adjustable to many different degrees of tightness due to the hook portions 27, 28 being capable of hooking to the belt all or substantially all along the length of the belt. Further, the belt is designed so that a long end 122 curls around the user across his/her entire front, extending toward the side opposite the injured arm (as shown in FIG. 3b) to help the user more easily fasten the belt. In the example of the belt adapted for an injured right arm (in FIG. 2b), the user may typically hold the long end 122 across his/her waist with his injured right arm/hand, while he/she uses the good arm/hand to pull the shorter end 123 under the long end. Then, the good arm attaches tab 28 to the underside of the long end 122 near the user's right side, and then presses the long end 122 against the user's left side to secure tab 27 against the belt outer surface. Depending on the waist size of the user, the belt may be wrapped around the waist and the hooking ends secured in various positions along the length of the belt, as necessary, to loosen or tighten the belt. The belt is preferably at least 3 inches wide from edge to edge and is preferably reinforced, to prevent belt roll.

In the preferred embodiment, upright support arm 24 is secured to the waist belt 22 at or near its central region (but typically sightly to the left or right for a left or right injured arm, respectively) via a rigid or semi-rigid connector 29, as shown in FIGS. 2b–2e. As shown in FIGS. 2c–e, the connector 29 comprises generally a long, thin waist plate 31, which conforms substantially to the circumferential contours of the back, and an upending plate 29 generally perpendicular to plate 31. Plate 129 and support arm lower end plate 129' may be curved in one or more directions to fit the back. Preferably, the plate 31 is attached to the belt by a firm hook and loop connection (using hook and loop that substantially covers the entire plate 31 and plate area 33 ), but may be attached by other means, such as sewing, adhesive, fasteners, latches, tape, etc., or may be integral with the belt. The support arm is preferably attached to the connector 29 preferably by means of a firm hook and loop connection, wherein the hook and loop materials (hook and loop securement means 32, 32') preferably cover all or substantially all of the plate 129 and of the lower end plate 129' of the arm. The support arm, may be attached by other means such as sewing, adhesive, fasteners, latches, tape, welding, etc., or may be integral with the connector and/or belt. Preferably, tightening the waist belt pulls the connector into firm contact with the back of the wearer to substantially immobilize the connector 29. This way, lateral movement of the upright support arm is sufficiently eliminated so long as a rigid connection between these two components (plate 129 and arm lower end plate 129') exists. The connection between the circumferential waist plate 31, a plate area 33 of the waist belt, and the lower end plate 129' may be further reinforced and secured by cover 34 (FIG. 2f). Cover 34 wraps around the combination of belt area 33, plate 31, and lower end plate 129' and is secured to itself and/or to the belt preferably by hook and loop connections, affording a more secure anchoring of the support arm and also affording padding between the waist plate 31—lower end plate 129' combination and the user.

Further, additional padding may be used on various portions of the support system, for example, a gel pack 37 may be inserted into or held on the plate 129 region, for example, by means of a wrap/cover 37', for cushioning the force of the plate 129 and/or the arm lower end plate 129' against the back. Also, cover 39 may be wrapped or otherwise attached to the curved portion 43 of the arm 24, for aesthetic reasons.

While the arm may extend integrally from the belt and/or connector, it is preferred, as described above, that the arm 24 is adjustably attached to the connector 29, for raising and lowering the support arm relative to the belt, and removably attached to the connector or belt, for disassembling the apparatus for transport and storage. While a hook and loop attachment is preferred, clamps, bolts, locking pins, or other fasteners may also be used, and points at which the connector and/or support arm contact the back of the wearer may be padded with foams or gel pads and then wrapped with soft fabrics, or other materials, to increase comfort. In the case of detachably secured components, the padding structures are preferably removable to facilitate disassembly. To strengthen the connection and/or increase stability of the upright support arm, additional structure may be implemented. For example, a diagonal stabilizing strap 35 may be attached between the waist belt and a point, generally the midpoint 36, on the upright support arm to further inhibit side-to-side motion of the support arm, as shown in FIG. 3d.

In the preferred embodiment, the upright support arm 24 comprises a lightweight, durable and inflexible arm extending up from the waist belt in a generally vertical orientation, as is also shown in FIG. 3a. The arm may be constructed of a lightweight metal, such as aluminum, or a hard plastic. Other alternatives may also be foreseeable to one skilled in the art.

In use, the upright support arm 24 preferably extends from the rigid connector 29 generally at or near the waist (preferably in the central region of a wearer's back but optionally toward the right or left side but behind the right or left arm, respectively) over the shoulder to a position generally forward of the chin and above the shoulder corresponding to the arm being suspended, as shown in FIGS. 3a–d. Preferably, the support arm is slightly curved so that it roughly follows the contours of the body as it extends from the back of the wearer to the front. However, it is important that the curved support provide sufficient clearance for, or separation from, the neck and shoulder regions so that these areas are not stressed or fatigued when the weight of the arm is applied to the arm sling apparatus.

Preferably, the length of the upright support arm 24 is adjustable to accommodate individuals of various heights, and this adjustment may be accomplished by the adjustable connection between the arm and the connector (lower end 129' and the plate 129). The arm 24 may be raised and lowered several inches on the plate 129 while still being securely held on the connector, so that a single sling apparatus 10 may fit many different individuals. Alternatively, the support arm 24 may be produced in several different sizes (S, M, L, XL). The distal end 42 of the arm 24 should extend forward enough so that any suspension straps 36 do not rest on or rub against the user, but instead extend through space to the cuffs/sling holding the user's arm. The arm 24 preferably curves in a "shepherd's hook" style up along the back and then approximately 180° at its top. The preferred arm 24 extends up along the user's back (typically in the range of about 14–25 inches for an adult, for example) and curves in a radius in the range of about 6–15 inches, and most preferably about 10–12 inches to stay distanced from the shoulder blade region, the top of the shoulder, the neck, and the front of the shoulder.

Above the shoulder, the distal end 42 of the support arm 24 preferably features an eyelet having an eyelet aperture 142, as shown in FIGS. 2b–e and 3c–d. In the preferred embodiment, the eyelet is fixedly and immovably secured to the support arm 24 such that total immobilization of the suspended arm may be achieved. However, in other embodiments, the eyelet may hang loosely or swivel to accommodate greater range of motion. Preferably, the length of the support arm is selected, or adjusted, so that the upper most extremity 124 of the arm is at least 1" above the shoulder, as shown in FIGS. 3a–d. Preferably, there is at least 1 inch, and most preferably at least 2 inches, of separation between all surfaces of the support member and the neck and shoulder so that pressure is not applied to these areas. In the preferred embodiment, the eyelet comprises the junction between the support frame assembly 20 and the suspension system 30 of the invented arm sling apparatus 10.

The suspension system 30 of the arm sling apparatus 10 comprises means adapted to encircle and/or contain the arm such that the weight of the arm may be transferred from the shoulder to the support frame. In the preferred embodiment, a plurality of suspension straps 36 are removably attached to the eyelet of the distal end 42, as shown in FIGS. 3a–d. The proximal ends 47 of these suspension straps 36 may be attached to the eyelet using any of a number of conventional, releaseable hooks 44 or clasps. Preferably, the suspending straps 36 comprise conventional, webbed straps 45 that may be flexed, but not stretched. However, some elasticity may be provided in the straps of various embodiments for comfort/shock-absorption or to permit increased range of motion. For example, a short length of elastic may be used as the proximal end 47 of the suspension straps 36, as this tends to reduce shock to the sling member and consequently to the user's arm, without making the straps 36 so elastic that their role as suspending and supporting devices is compromised. The straps 36 are preferably generally flat, but may also be round or other shapes, and may include cords, tethers, cables, or other elongated members. The straps of the preferred embodiment may be lengthened or shortened via any of a number of conventional adjustment mechanisms 46, an example of which is demonstrated in FIG. 4a. Preferably, the distal ends 48 of the suspension straps are secured (one each) by a buckle or other fastener 49 to a plurality of cuffs 50 adapted to encircle the arm, as shown in FIGS. 4b. In operation, the suspension straps 36 and cuffs 50 form a suspension system (see FIG. 1) wherein the weight of the arm may be transferred to the hips and back via the support frame 20. This cooperation between suspension system 30 and support frame 20 allows the arm sling apparatus to lift the arm into a particular position relative to the body to unload the shoulder and neck.

The cuffs 50 of the arm support system comprise a band 52 of material adapted to wrap around the circumference of the arm at various points, as shown in FIG. 4b. In the preferred embodiment, three cuffs are positioned on the arm in generally the following areas: the bicep, the forearm (adjacent the elbow) and the wrist, as shown in FIGS. 1 and 3. The cuffs are preferably padded using layered fabrics, foam or other cushioning methods for increased wearing comfort. At opposite ends of the cuffs, tabs of hook and loop material 28, 27' are fixedly secured to the opposing surfaces, as is also shown in FIG. 4b. The tabs are arranged such that when the cuff is wrapped about the arm, the hook material 28' engages the loop material 27' to secure the cuff. Alternatively, the cuffs may be secured about the arm using alligator clips, clasps or other fastening means. Other embodiments of the suspension system may include a single, wider wrap or sleeve 50 that extends around substantially all of the forearm on three sides, and attaches to the eyelet as shown in FIG. 5a. Other sling members may be designed, encircling or otherwise engaging various portions of the arm, for example, straps, cuffs, sleeves, platforms, shirt sleeve attachments, connectors to wrapping tape on the arm, connectors to arm casts, etc. In addition, some embodiments of the arm sling apparatus 10 may include a pillow 50 positioned between the arm and torso for additional comfort, as shown in FIG. 5b.

Opposite (below) the suspension strap attachment, a second strap, a restraining or immobilization strap 60, is preferably fixedly secured to the cuff, as shown in FIG. 4c fastener 49'. The immobilization strap extends between the cuff and waist belt to anchor the cuff and, therefore, the arm relative to the body, as shown in FIGS. 1 and 3. In some embodiments, a plurality of immobilization straps may be fixedly attached to each of the cuffs to permit further immobilization (not shown).

In the preferred embodiment, the immobilization straps (one for each cuff) are removably secured to the waist belt via belt-encircling straps 62 and 60 alligator clips 64 or other detachable hooks or clasps, as shown in FIGS. 3b–d. As with the suspension straps, the lengths of the immobilization straps are preferably adjustable using conventional techniques and equipment, such as adjustor 66. This way, the extent of immobilization may be selected or adjusted as necessary. In addition belt-encircling straps 62 may be slid longitudinally on the belt to adjust the direct and location of the force applied by the immobilization straps. In combination, the restraining/immobilizing straps restrict the amount of downward and outward (away from the body) motion of the arm, respectively. In addition, the immobilization straps may be tightened so that upward motion of the arm and/or lateral movement across the body is restricted or prevented.

Figure 6A:
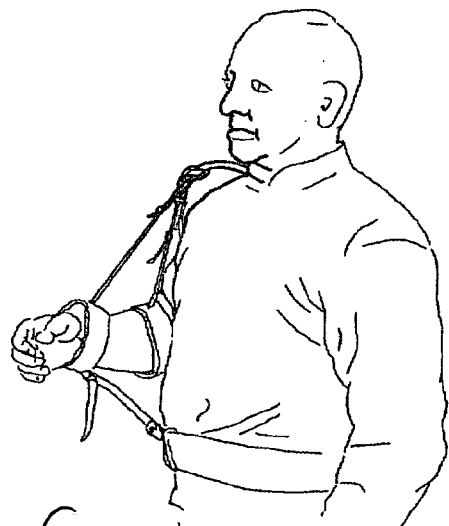
FIGS. 6a–d are perspective views of the sling of FIG. 1 demonstrating various degrees of mobility and/or activity facilitated by the system as they apply to various support applications.
Figure 6B:
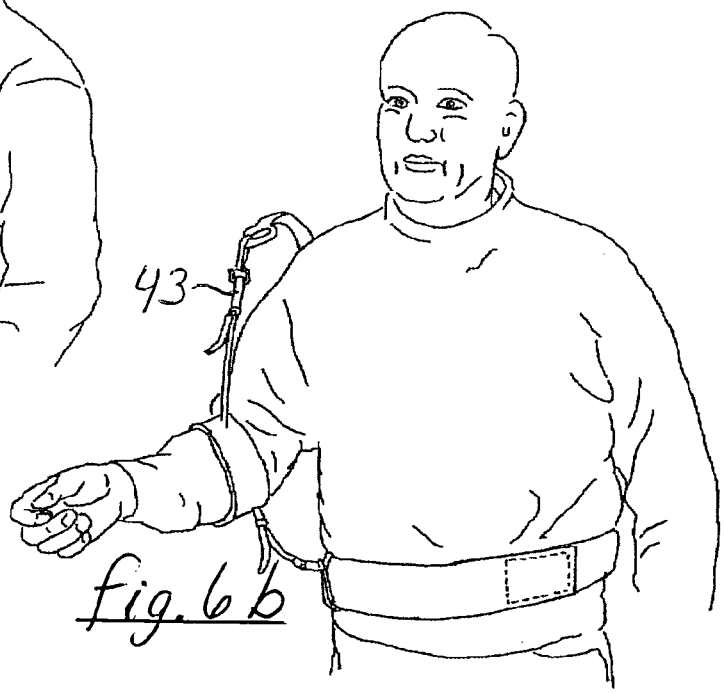
Figure 6C:
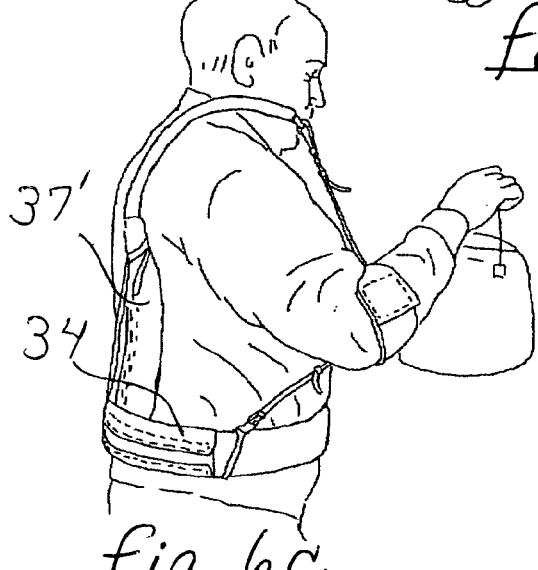
Figure 6D:
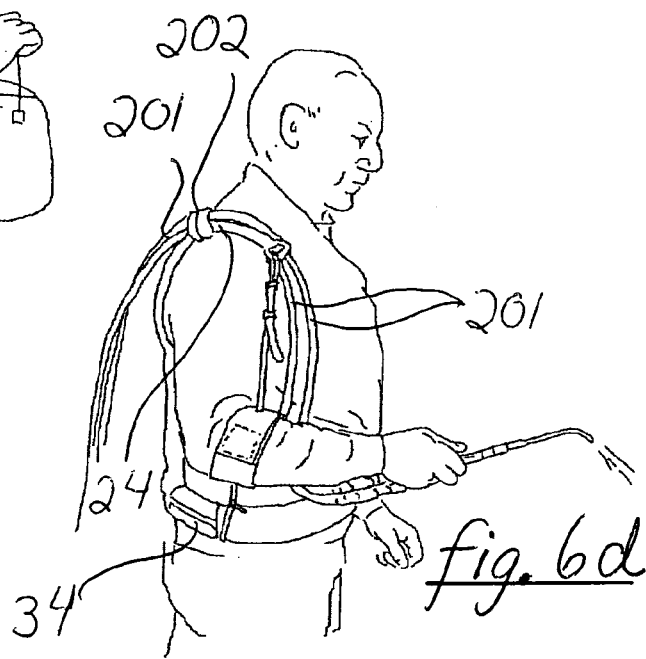

Typically, the invented arm sling apparatus will find application to situations in which an arm or shoulder has been injured and requires rest. For example, the apparatus may be worn after shoulder surgery is performed to immobilize the arm and allow the shoulder to heal properly, as shown in FIG. 1. In addition, the sling may be helpful for rehabilitation purposes wherein increasing amounts of movement and/or load-bearing may be permitted to strengthen the arm and/or shoulder. The arm sling may also be worn following the breaking of an arm. In such situations, whether a cast is worn or not, at least minimal immobilization of the arm is often required. The invented arm sling apparatus facilitates restriction of arm motion without placing stress on the shoulder or neck regions as is common with many existing slings. In addition to these limited examples, other useful applications of the invented apparatus may be foreseeable to one skilled in the art. For example, the apparatus may be worn to support the arm during various activities requiring repetitive or prolonged stresses to the arm and/or shoulder musculature, particularly those in which the arm may be in an outstretched or weak position, as shown in FIGS. 6a–d. Examples of such activities are painting, sculpting and other arts, welding, gardening, etc. FIG. 6d illustrates a sling apparatus according to one embodiment of the invention being used by a welder, wherein the welding hose 201 is supported by the support arm 24 and attached to the support arm 24 by a wrap/fastener 202. This illustrates how the weight of an object or tool may be minimized by being attached to and/or supported by the support arm, and how the object or tool in this way is also properly kept in place during use to guard against stress and injury to the user.

While the term "strap" is used herein for suspension straps and immobilization straps, it is to be understood that these components are not necessarily limited to being flat and not necessarily limited to being made of cloth or webbing. The term "strap member" in the claims may also include various fastening devices, such as elongated and/or adjustable clips, tethers, brackets, cords, strings, loops, etc. that will serve in the capacity of the suspension straps and immobilization straps extending between the arm and the sling member, and extending between the sling member and the belt, respectively. Further, the sling member and the suspension strap(s) may be combined into a single unit that hangs from the support arm and encircles and/or supports the arm. Also, when there are a plurality of strap members being used, they need not all be identical.

While the preferred embodiments include a single support arm, embodiments may also include more than one support arm, either on both sides of the person or even on a single side. Further, there may be additional items hung from or supported by the support arm, belt, and/or sling member.

Although this invention has been described with reference to particular means, materials and embodiments, it is to be understood that the invention is not limited to these disclosed particulars, but extends instead to all equivalents within the scope of the following claims.

I claim:

1. An arm sling apparatus comprising;
   a belt for encircling a user's torso and having a front portion and a rear portion;
   a support arm extending up from, and supported by, the rear portion of the belt and curving forward so that a distal end of the support arm is generally above the front portion of said belt;
   a sling member adapted to engage a user's arm and connected to the distal end of the support arm;
   wherein the support arm is sized and configured to curve over, but not touch, the user's shoulder, and wherein the arm sling apparatus is configured to have no contact with the neck and shoulders of the user,
   so that the load of the user's arm in the sling member is transferred by the support arm to the rear portion of the belt and not to the neck and shoulders.

2. An arm sling apparatus as in claim 1, wherein the sling member is a cuff adapted to encircle a portion of the user's arm.

3. An arm sling apparatus as in claim 1, wherein the sling member is a broad sling adapted to receive substantially all of the user's forearm.

4. An arm sling apparatus as in claim 1, further comprising a strap member extending between the support arm and the sling member to connect the sling member to the support arm.

5. An arm sling apparatus as in claim 4, further comprising a plurality of said strap members.

6. An arm sling apparatus as in claim 5, wherein said strap members are adjustable in length.

7. An arm sling apparatus as in claim 1, comprising a plurality of sling members.

8. An arm sling apparatus as in claim 7, further comprising a plurality of immobilization strap members, at least one of said immobilization strap members being connected to each of said sling members and extending between each said sling member and the belt.

9. An arm sling apparatus as in claim 1, further comprising one or more immobilization strap members connected to and extending between the sling member and the belt.

10. An arm sling apparatus as in claim 9, wherein said immobilization strap members are adjustable in length.

11. An arm sling apparatus as in claim 9, wherein said immobilization strap members are moveable longitudinally along the belt.

12. An arm sling apparatus as in claim 9, wherein said immobilization strap members are slidable longitudinally along the belt.

13. An arm sling apparatus as in claim 1, wherein said support arm has a lower end that is generally straight and an upper end that curves to accomplish said placement of the distal end over the front portion of the belt.

14. An arm sling apparatus as in claim 1, wherein said support arm is adapted to have a length and a curvature in its upper end so that said support arm upper end does not contact the user.

15. An arm sling apparatus as in claim 1, wherein said support arm is removable from said belt and adjustable to various locations on the belt.

16. An arm sling apparatus as in claim 1, further comprising a gel pack and a gel pack attachment system connected to a lower end of the support arm near the rear portion of the belt for placing the gel pack between the support arm and the user's back.

17. An arm sling apparatus as in claim 1, wherein the support arm curves forward at its top end in a radius of 6–15 inches to curve over a user's shoulder.

18. An arm sling appartus as in claim 1, wherein the support arm is rigid.

19. An arm sling apparatus as in claim 1, wherein the support arm is inflexible.

20. An arm sling apparatus as in claim 1, where a suspension system connects the sling member to the distal end of the support arm to suspend the sling member from the distal end; and
   wherein the support arm is configured so the distal end holds said suspension system away from the user so that suspension system does not rest on the user.

21. An arm sling apparatus comprising;
   a belt for encircling a user's torso and having a front portion and a rear portion;
   a support arm supported by and extending up from the rear portion of the belt, the support arm configured to curve forward over the user's shoulder;
   a sling member adapted to engage a user's arm and connected to the distal end of the support arm;
   wherein the support arm is configured so that all surfaces of the support arm are spaced at least one inch from the user's shoulder and neck, and the arm sling apparatus is adapted to not touch a user's shoulder and is adapted to not touch a user's neck.

* * * * *